United States Patent [19]

Bergthaller et al.

[11] 4,067,741
[45] Jan. 10, 1978

[54] HARDENING PHOTOGRAPHIC LAYERS CONTAINING SILVER HALIDE WITH A 1-SULPHONYL-4-AMINO-PYRIDINIUM SALT

[75] Inventors: Peter Bergthaller, Cologne; Wolfgang Himmelmann, Leverkusen; Lothar Rosenhahn, Cologne, all of Germany

[73] Assignee: AGFA-Gevaert, A.G., Leverkusen, Germany

[21] Appl. No.: 733,759

[22] Filed: Oct. 19, 1976

[30] Foreign Application Priority Data

Oct. 24, 1975  Germany ............................. 2547589

[51] Int. Cl.² ............................................... G03C 1/30
[52] U.S. Cl. .......................................... 96/111; 96/67; 96/76 R; 96/77; 260/112 R; 260/117; 106/125; 427/338; 526/317

[58] Field of Search ................... 96/111, 76 R, 77, 67, 96/50 PT; 260/117, 112; 427/338; 526/317; 106/125

[56] References Cited

U.S. PATENT DOCUMENTS

| | | | |
|---|---|---|---|
| 2,816,125 | 12/1957 | Allen et al. | 96/111 |
| 2,950,197 | 8/1960 | Allen et al. | 96/111 |
| 2,964,404 | 12/1960 | Burness | 96/111 |
| 3,839,042 | 10/1974 | Silverman | 96/111 |
| 3,880,665 | 4/1975 | Himmelmann | 96/111 |

*Primary Examiner*—Won H. Louie, Jr.
*Attorney, Agent, or Firm*—Connolly and Hutz

[57] ABSTRACT

1-Sulphonyl-4-amino-pyridinium salts are used as quick acting hardeners for protein-containing layers, in particular gelatine layers, for photographic purposes.

10 Claims, No Drawings

HARDENING PHOTOGRAPHIC LAYERS CONTAINING SILVER HALIDE WITH A 1-SULPHONYL-4-AMINO-PYRIDINIUM SALT

This invention relates to a process for hardening photographic layers which contain protein, preferably gelatine.

Numerous substances have already been described as hardeners for protein, in particular for gelatine. These include, for example, metal salts such as chromium, aluminium or zirconium salts; aldehydes and halogenated aldehyde compounds, in particular formaldehyde, dialdehydes and mucochloric acid; 1,2- and 1,4-diketones such as cyclohexane-1,2-dione and quinones; chlorides of dibasic organic acids; anhydrides of tetracarboxylic acid; compounds having several reactive vinyl groups, such as vinyl sulphones, acrylamides; compounds having at least two readily decomposable heterocyclic 3-membered rings such as ethylene oxide and ethylene imine; polyfunctional methane sulphonic acid esters and bis-α-chloroacylamide compounds.

High molecular weight hardeners have recently become known, for example polyacrolein and its derivatives or copolymers and alginic acid derivatives, which are used especially as hardeners which are confined to the layers containing them.

Many of the compounds mentioned above are, however, unsuitable particularly for photographic purposes. Some of them are photographically active and for this reason unsuitable for hardening photographic materials while others cannot be used because they have such a deleterious effect on the physical properties of gelatine layers such as their brittleness. Others again bring about discolorations or a change in pH during the hardening reaction. Moreover, when hardening photographic layers it is particularly important that the degree of hardening should rapidly reach its maximum after drying so that the material being hardened will not undergo a continuous change in its permeability to the developer solution as is the case, for example, with mucochloric acid or formaldehyde.

Some cross-linking agents for gelatine, such as ethylene imine compounds, for example, have a damaging effect on the skin and are therefore in any case unsuitable on physiological grounds.

It has also long been known to use trichlorotriazine and dichloroaminotriazines as hardeners. The disadvantage of these compounds is their relatively high vapour pressure and physiological action. Water-soluble derivatives which contain carboxylic and sulphonic acid groups and which have been obtained by the reaction of cyanuric chloride with 1 mol of a diaminoalkyl or diaminoaryl sulphonic acid or carboxylic acid do not show these disadvantages and have therefore recently been proposed as hardeners. Their practical utility is, however, limited, because, as a result of their high solubility, they decompose when left to stand in aqueous solutions and therefore rapidly lose their activity. Hydroxydichlorotriazine has also been proposed as hardener. Finally, when choosing a hardener from photographic layers containing gelatine it is of the greatest importance, both for the preparation of the materials and for their processing, to be able to predetermine the onset of the cross-linking reaction to a certain extent, for example, by choice of the drying temperature or choice of the pH.

Compounds having two or more acrylic acid amido or vinylsulphone groups in the molecule are also known as hardeners for photographic gelatine layers, for example divinylsulphone, arylene-bis-vinylsulphones, N,N',N''-trisacryloylhydrotriazine and methylene-bis-vinylsulphonamide.

Although these compounds harden effectively after some time, they are only sparingly soluble in water and consequently the layers may harden unevenly.

The consequences of these undesirable properties of known hardeners described above are very important from a photographic point of view since important photographic properties such as the gradation and sensitivity and in many cases also the silver covering power depend on the degree of cross-linkage of the layer forming colloid and alter during storage. Although this disadvantage can be attenuated by briefly after-treating the solidified layer with ammonia or an amine, it cannot be completely overcome by this method. Added to this is the disadvantage that aliphatic divinylsulphones have a damaging effect on the skin.

Another class of compounds which have become known as hardeners with a very good gross-linking action on gelatine and high molecular weight compounds or mixtures of compounds containing carboxyl groups and amino groups are the carbamoyl pyridinium salts. One disadvantage of these hardeners is that they are liable to split off pyridine or pyridine derivatives during their reaction with the binder, and their range of commercial application is thereby restricted.

It is an object of the present invention to provide quick acting hardeners for protein-containing layers, in particular gelatine layers, for photographic purposes, which hardeners do not have the technological disadvantages of the known compounds.

A process for hardening layers containing protein, in particular gelatine, has now been found which is characterised in that 1-sulphonyl-4-amino-pyridinium salts are used as hardeners.

The 1-sulphonyl-4-aminopyridinium salts used as hardeners may be represented by the following general formulae:

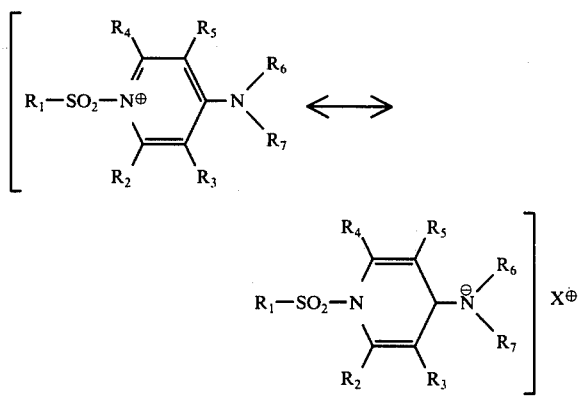

in which
$R_1$ represents alkyl with 1 to 4 carbon atoms, aryl such as phenyl, tolyl or mesityl which may be substituted by halogen, e.g. by chlorine or bromine, or aralkyl such as benzyl or phenethyl, a sulphoalkyl or alkenyl group having 3 to 4 carbon atoms or a disubstituted amino group, e.g. a dialkylamino group such as dimethylamino, diethylamino or dipropylamino;

$R_2$ represents hydrogen or alkyl such as methyl or ethyl;

$R_3$ may have the same meaning as $R_2$ or it may represent an aminocarbonyl group or together with $R_2$ it may represent the atoms required to complete a condensed benzene ring;

$R_4$ and $R_5$ represent hydrogen or alkyl such as methyl or ethyl;

$R_6$ represents hydrogen, alkyl with 1 to 3 carbon atoms, aralkyl such as benzyl or phenylethyl or sulphoalkyl such as sulphoethyl and sulphopropyl;

$R_7$ represents hydrogen or alkyl with 1 to 3 carbon atoms or together with $R_6$ and the nitrogen atom it may represent the atoms required to complete a saturated 5- or 6-membered heterocyclic ring, e.g. a pyrrolidine, piperidine or morpholine ring, $X^-$ represents an anion such as $Cl'$, $Br'$, alkyl-$SO_3$ such as methyl-$SO_3'$ or ethyl-$SO_3'$ or a hard anion from the group $ClO_4'$, $BF_4'$, $PF_6'$ or $SbF_6'$; $X^-$ is absent when either $R_1$ or $R_6$ contains a sulpho group.

The following compounds are typical examples of 1-sulphonyl-4-aminopyridinium salt used as hardeners according to the invention:

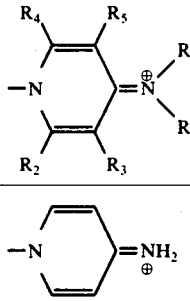

| Compound | $R_1SO_2-$ | $R_2$   $R_3$ | $X^\ominus$ | Fp. (° C) |
|---|---|---|---|---|
| 1 | $CH_3SO_2-$ | 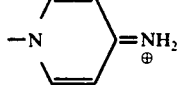 | $Cl^\ominus$ | >145° |
| 2 | " | " | $CH_3SO_3^\ominus$ | 170-74° |
| 3 | " | " | $ClO_4^\ominus$ | 169-71° |
| 4 | " | 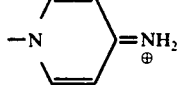 | $Cl^\ominus$ | 132° |
| 5 | " | 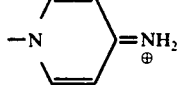 | $Cl^\ominus$ | 123-25° |
| 6 | " | " | $CH_3SO_3^\ominus$ | >141° |
| 7 | " | 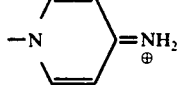 | $Cl^\ominus$ | 120-21° |
| 8 | " | 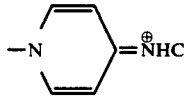 | $Cl^\ominus$ | 134° |
| 9 | " | 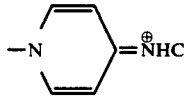 | $Cl^\ominus$ | 121-22° |
| 10 | " | 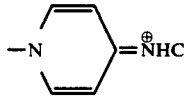 | $Cl^\ominus$ | >110° |
| 11 | " | " | $CH_3SO_3^\ominus$ | >120° |
| 12 | " | 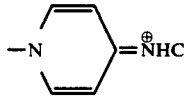 | $Cl^\ominus$ | 140-43° |
| 13 | " | " | $CH_3SO_3^\ominus$ | >140° |
| 14 | " | 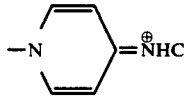 | $Cl^\ominus$ | >90° |

-continued
$$\underset{R_2\ \ R_3}{\overset{R_4\ \ R_5}{\underset{\|}{\underset{N}{\bigcirc}}}}\overset{R_6}{\underset{R_7}{N^{\oplus}}}$$
| Compound | R₁SO₂— | (pyridinium moiety) | X⊖ | Fp. (° C) |
|---|---|---|---|---|
| 15 | " | 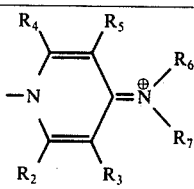 | Cl⊖ | >100° |
| 16 | " | 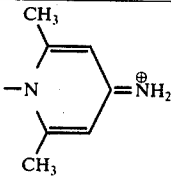 | Cl⊖ | 110–11° |
| 17 | " | 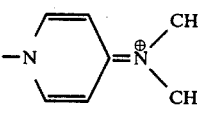 | Cl⊖ | 59° |
| 18 | " | 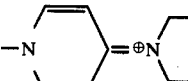 | — | >145° |
| 19 | " | 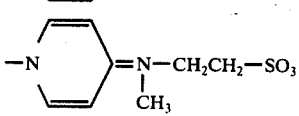 | Cl⊖ | 53–55° |
| 20 | " | " | ⊖ | 80° |
| 21 | " | 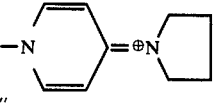 | Cl⊖ | 89–91° |
| 22 | " | 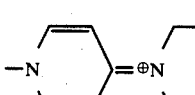 | Cl⊖ | >90° |
| 23 | " | 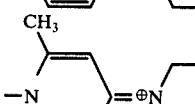 | Cl⊕ | 122° |
| 24 | C₂H₅SO₂— | 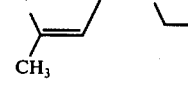 | Cl⊖ | >110° |
| 25 | CH₃(CH₂)₃SO₂— | " | Cl | 110° |
| 26 | 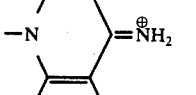 | " | Cl | 80–120° |
| 27 | Cl—CH₂CH₂—SO₂— | " | Cl | 118° |
| 28 | 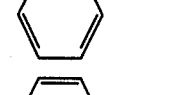 | " | Cl | 182–84° |
| 29 | 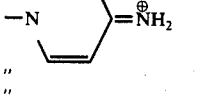 |  | Cl⊖ | 107–09° |

-continued

| Compound | R₁SO₂— | (pyridinium structure with R₂–R₇) | X⁻ | Fp. (° C) |
|---|---|---|---|---|
| 30 | 4-CH₃-C₆H₄-SO₂— | " | Cl⁻ | 115–20° |
| 31 | " | —N◯=N-morpholine | Cl⁻ | >138° |
| 32 | C₆H₅-CH₂SO₂— | —N◯=⁺NH₂ | Cl⁻ | >115° |
| 33 | " | —N◯=⁺N-morpholine | Cl⁻ | 173° |
| 34 | C₆H₅-SO₂— | —N◯=⁺NH₂ | Cl⁻ | >128° |
| 35 | 2,6-Cl₂-C₆H₃-SO₂— | —N◯=⁺NH₂ | Cl⁻ | 118–122° |
| 36 | 2,4,6-(CH₃)₃-C₆H₂-SO₂— | —N◯=NH₂ | Cl⁻ | 143° |
| 37 | | | | |
| 38 | " | —N◯=N(CH₃)₂ | Cl⁻ | 137° |
| 39 | " | —N◯(2,6-diCH₃)=N-morpholine | Cl⁻ | 134° |
| 40 | " | —N◯=NH-CH₂CH₂-SO₃ | — | >130° |
| 41 | O₃S—(CH₂)₃—SO₂— | —N◯=⁺N(CH₃)₂ | — | >110° |
| 42 | CH₃—SO₂— | —N◯(3-CONH₂)=NH₂ | | |

The 1-sulphonyl-4-aminopyridinium salts according to the present invention are particularly suitable for Numerous structural variations of 1-sulphonyl-4-amino-pyridinium salts are available. The components used for the sulphonyl portion may be $R_1SO_2$-aliphatic or aromatic or arylaliphatic sulphochlorides, sulphofluorides, sulphobromides or sulphonic acid anhydrides, aliphatic or aromatic cyclic disulphonic acid anhydrides, dialkylsulphamide chlorides or chlorosulphonylacylanilines but not chlorosulphonic acid esters. The following compounds are particularly suitable: Methanesulphochloride, ethanesulphochloride, 2-chloroethanesulphochloride, propane-2-sulphochloride, butane-1-sulphochloride, toluene--sulphochloride, benzenesulphochloride, toluene-4-sulphochloride, toluene-2-sulphochloride, 3-chlorobenzene-sulphochloride, 2,6-dichlorobenzene-sulphochloride, mesitylene sulphochloride, methanesulphonic acid anhydride, benzenesulphonic acid anhydride, benzene-1,2-disulphonic acid anhydride, propene-1,3-disulphonic acid anhydride, 2-methylpropene-1,3-disulphonic acid anhydride, dimethylsulphamido chloride, morpholine-N-sulphochloride, phthalimide-N-sulphochloride and acetanilide-N-sulphochloride.

Any of the compounds not obtainable commercially can easily be prepared by methods well known from the literature.

The components used for the pyridinium portion may be practically any 4-aminopyridines provided they are not substituted by strongly electrophilic substituents either in the nucleus or directly on the amino group. Particularly suitable are 4-aminopyridines carrying one or more alkyl groups as substituents in the nucleus or on the amino group.

The following compounds are mentioned as examples: 4-Aminopyridine, 4-methylaminopyridine, 4-ethylaminopyridine, 4-isopropylaminopyridine, 4-n-butylaminopyridine, 4-cyclohexylaminopyridine, 4-anilinopyridine, 4-dimethylaminopyridine, 4-pyrrolidinopyridine, 4-piperidinopyridine, 4-morpholinopyridine, 4-amino-2-methylpyridine, 4-amino-3-methylpyridine, 4-amino-3-ethylpyridine, 4-amino-3-isopropylpyridine, 4-amino-2,6-dimethylpyridine, 4-amino-3,5-dimethylpyridine, 4-amino-2-methyl-5-ethylpyridine, 4-amino-2,3,5,6-tetramethylpyridine, 4-methylamino-3-ethylpyridine, 4-dimethylamino-3-methylpyridine, 4-amino-3-ethoxypyridine, 4-morpholino-2,6-dimethylpyridine, 4-aminoquinoline, N-(4)-pyridyltaurine and 4-aminonicotinamide.

These compounds are also either available commercially or easily prepared by methods well known from the literature.

4-Amino-2,6-lutidines are a special case. They can be directly obtained from 2,6-lutidine-N-oxide via 4-chloro-2,6-lutidine by a particularly simple method and in high yields (T. Kao, Yakugaku Zasshi 75 (1955) 1236).

Introduction of special anions X into the sulphonyl-4-aminopyridinium salts can also be carried out subsequently by anion exchange, e.g. with perchlorate in methanolic solution, and rarely gives rise to any problems.

Reaction of 4-aminopyridines with the sulphonyl compounds can be carried out in practically any aprotic solvents which do not have a marked basic character but it can also be carried out in systems which have only a low concentration of protic solvents, e.g. in lower alcohols provided the reaction time is not too long. Particularly suitable solvents are acetone, ethyl acetate, dioxane, tetrahydrofuran, dimethylformamide, acetonitrile, dichloromethane, chloroform, ethyl glycol acetate and 1,2-dichloroethane. In many cases the reaction may even be carried out in pyridine.

Most of the new compounds are thermally stable up to temperatures above 100° C but almost all of the compounds melt exothermally, that is to say with decomposition and often over a fairly wide temperature range.

Hydrolysis of the new compounds is strongly dependent on the pH and is powerfully accelerated both by high and by low pH values, the region of optimum stability in aqueous solution being between pH 4 and pH 7. It has not yet been established with certainty whether in aqueous solutions the compounds exist as sulphonyl-4-aminopyridinium salts. Since most of them are slightly acid in reaction in aqueous solution, they could conceivably be in the form of sulphonylpyridone-4-imines, provided the amine nitrogen has a free hydrogen atom. It is also possible that the compounds take up water to change into uncharged pseudobases of the formula:

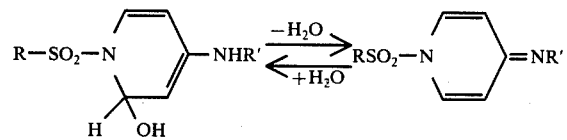

as assumption for which evidence is in some cases provided by the proton resonance spectra.

Similar reactions are already known, particularly among compounds of the quinoline series. 2-hydroxy-1-alkoxycarbonyl-1,2-dihydroquinoline has been disclosed in U.S. Pat. Nos. 3,389,142 and 3,452,140.

This may be one of the reasons for the surprising stability of the new compounds in protic solvents such as water or methanol in which, once formed, the new compounds are astonishingly stable, in many cases even for several days.

The process of preparation of the 1-sulphonyl-4-aminopyridinium salts according to the invention will now be explained with the aid of the following Examples:

EXAMPLE OF PREPARATION 1 (COMPOUND 1)

9.5 g (0.1 mol) of 4-aminopyridine are introduced with stirring into a solution of 12.6 (0.11 mol) of methane sulphochloride in 100 ml of anhydrous acetone at 0° C with exclusion of moisture. A white crystalline precipitate forms while 4-aminopyridine goes into solution. After the addition of 5 ml of isopropanol, this precipitate is suction filtered and dried over calcium chloride in a desiccator.

The yield is 18.7g which is 90% of the theory with a melting point of 145° C with decomposition.

Calculated on the basis of $C_6H_9ClN_2O_2S$: C, 34.53%; H, 4.32%; N, 13.43% Found: C, 34.3%; H, 4.3%; N, 13.4%; Cl, 17.3%.

NMR spectrum: Determined on fresh sample in $D_2O$ 2.8 ppm (1 proton), 3.7 ppm (1 proton) 4.65 ppm (3 protons), 6.7–8.5 ppm (4 protons) (multiplet)

EXAMPLE OF PREPARATION 2 (COMPOUND 2)

4.7 g (0.05 mol) of 4-aminopyridine are added to a solution of 8.7 g (0.05 mol) of methane sulphonic acid anhydride in 100 ml of anhydrous acetone at 0° C. The product, which precipitates almost instantly in the form of a salt, is suction filtered and dried under vacuum. The yield is 13 g which is 97% of theory and the melting point is 170° to 174° C with decoposition.

Calculated on the basis of $C_7H_{12}N_2O_5S_2$: C, 31.3%; H, 4.5%; N, 10.4%; S, 23.9%. Found: C, 32.0%; H, 4.5%; N, 10.7%; S, 23.1%.

EXAMPLE OF PREPARATION 3 (COMPOUND 3)

2 g of Compound 1 are dissolved in 7 ml of distilled water and 10 ml of methanol. The solution instantly gives rise to white needles when introduced into 10 ml of a 2 molar methanolic sodium perchlorate solution. The needles are suction filtered, washed with a little methanol and dried.

The yield is 2.5 g which is 95% of the theory with a melting point of 169° to 171° C with decomposition.

EXAMPLE OF PREPARATION 4 (COMPOUND 38)

To a solution cooled to 0° C of 10.9 g (0.05 mol) of mesitylene sulphochloride in 50 ml of anhydrous acetone are added 6.1 g (0.05 mol) of 4-dimethylaminopyridine in 30 ml of acetone. The product, which precipitates instantly, is suction filtered and dried under vacuum.

The yield is 15.5 g which is 91% of the theory with a melting point of 137° C with decomposition.

EXAMPLE OF PREPARATION 5 (COMPOUND 41)

9.5 g (0.1 mol) of 4-dimethylaminopyridine are introduced at −5° C to 0° C into a solution of 18.6 g (0.1 mol) of propane-1,3-disulphonic acid anhydride (prepared by the method of Geiseler and Kuschmiers; Chem. Ber. 91 (1958), page 1514) in 100 ml of anhydrous acetone with stirring and exclusion of moisture. Pyridinium sulphobetaine rapidly precipitates as a white crystalline solid. It is treated with a small quantity of isopropanol, suction filtered and dried under vacuum.

The yield is 23 g which is 82% of the theory. Melting starts at 140° C with decomposition.

The compounds according to the invention may be added to the protein layers as aqueous or alcoholic solutions or solutions in a mixture of the two solvents before they are cast. The protein layers to which they are added harden either extremely rapidly or moderately rapidly, depending on the structure of the compound and the concentration in which it is employed but, even with the most inert compounds, hardening is completed within 1 to 2 days so that no after hardening effects need be expected. The most rapid hardening is obtained with those 1-alkanesulphonyl-4-aminopyridinium salts which are derived from alkanesulphochlorides, somewhat slower hardening with 1-arylsulphonyl-4-aminopyridinium salts and with alkanesulphonyl-4-aminopyridinium salts which are derived from 2-substituted 4-aminopyridines, and the slowest hardening with 1-sulphamoyl-4-aminopyridinium salts.

One particularly advantageous method of employing the hardeners consists of casting the unhardened films and then coating them, optionally when already dry, with a solution of the hardening compounds. Thickeners may be added to these solutions to improve their pouring properties. Since the compounds used according to the invention react fairly rapidly with proteins, the thickeners used are advantageously hydrophilic polymers which do not react with the hardeners according to the invention and at the same time have film forming properties. Examples of suitable thickeners include celluloses and cellulose derivatives, polyalkylene oxides, polyvinyl alcohol and its derivatives, polyvinyl sulphonic acid, styrene sulphonic acid and copolymers thereof, sulphoalkyl substituted polyacrylates, polymethacrylates, polyacrylamides, polymethacrylamides and the like. Another method of applying the compounds according to the invention consists of bathing the photographic materials in aqueous solutions of the compounds as part of the photographic process, for example photographic layers which have not yet been hardened or only slightly hardened may be bathed in such solutions before development.

The compounds described here may be used either singly or as mixtures. They may advantageously be used for hardening photographic layers which, in addition to gelatine, also contain other carboxyl-containing homopolymers and copolymers as binders. It is assumed that the compounds used according to the invention are capable of bringing about cross-linking of gelatine and of polymers containing carboxyl groups.

The term photographic layers is used in this context quite generally to cover any layers used in photographic materials, for example, light-sensitive silver halide emulsion layers; protective layers; filter layers; anti-halation layers; back coating layers or any photographic auxiliary layers in general.

As examples of light-sensitive emulsion layers for which the hardening process according to the invention is eminently suitable may be mentioned those layers which are based on unsensitized emulsions, X-ray emulsions and other spectrally sensitized emulsions. The hardening process according to the invention has also proved to be suitable for hardening gelatine layers used for various black and white as well as colour photographic processes such as negative, positive and diffusion transfer processes or printing processes. The process according to the invention has proved to be particularly advantageous for hardening combinations of photographic layers which are intended for carrying out colour photographic processes, for example those which have emulsion layers containing colour couplers or emulsion layers intended to be treated with solutions which contain colour couplers.

The effect of the compounds used according to the invention is not impaired by the usual photographic additives. The hardeners are also unaffected by photographically active substances such as water-soluble and emulsified water-insoluble colour components, stabilisers, sensitizers and the like. Moreover, they have no deleterious effect on the light-sensitive silver halide emulsions.

The compounds may also be combined with any compounds belonging to previously known classes of hardeners, for example, formalin, mucochloric acid, triacryloformal, bisvinylsulphones, bisvinylsulphonamides, dialdehydes or bischloroacetamides or inorganic salts such as trivalent chromium, trivalent aluminium or zirconium salts.

The light-sensitive components of the emulsion layers may be any of the known silver halides such as silver chloride, silver iodide, silver bromide, silver iodobromide, silver chlorobormide, silver chloroiodobromide or the like. The emulsion may be chemically sensitized with noble metal compounds, e.g. compounds of ruthenium, rhodium, palladium, iridium, platinum, gold and the like such as ammonium chloropalladate, potassium chloroplatinate, potassium chloropalladite, or potassium chloroaurate. They may also contain special sensitizing agents in the form of sulphur compounds, tin(II) salts, polyamines or polyalkylene oxide compounds. The emulsions may also be optically sensitized with cyanine dyes, merocyanine dyes or mixed cyanine dyes.

Finally, the emulsions may contain various couplers such as colourless couplers or coloured couplers; stabilizers such as mercury compounds, triazole compounds, azaindene compounds, benzothiazolium compounds or zinc compounds; wetting agents such as dihydroxyalkanes; substances which improve the film forming properties, e.g. water dispersible, particulate high molecular weight polymers of the kind obtained by emulsion polymerisation of alkyl acrylate, alkyl methacrylate/acrylic acid or methacrylic acid copolymers; also styrene/maleic acid copolymers, styrene/maleic acid anhydride semialkyl ester copolymers; coating agents such as polyethyleneglycol lauryl ether and various other photographic additives.

In addition to gelatine, the layers may contain other hydrophilic colloids such as colloidal albumen, agar-agar, gum arabic, dextrans, alginic acid, cellulose derivatives, e.g. cellulose acetate which has been hydrolysed up to an acetyl content of from 19 to 26%, polyacrylamides, imidatised polyacrylamides, zein, vinyl alcohol polymers containing urethane/carboxylic acid groups or cyanoacetyl groups such as copolymers of vinyl alcohol and vinyl cyanoacetate, polyvinyl alcohols, polyvinyl pyrrolidones, hydrolysed polyvinyl acetates, polymers of the kind obtained by the polymerisation of proteins or saturated acylated proteins with monomers containing vinyl groups, polyvinylpyridines, polyvinylamines, polyamino ethylmethacrylates and polyethyleneimines.

The concentrations in which the hardeners according to the invention are used may vary within wide limits and depend mainly on the particular hardening compound used.

Satisfactory results are obtained with quantities of from 0.5 to 10% by weight and preferably 1 to 5% by weight of hardening compound based on the dry weight of binder.

The hardening compounds according to the invention are thus distinguished by a hardening reaction which proceeds very rapidly and without side effects. This property makes the compounds particularly suitable for the preparation of very hard photographic layers with a clearly defined and low degree of swelling. All that is needed to achieve this result is to treat the dry or slightly swelled photographic layer with a solution of the hardening compounds for a short time and then to dry it rapidly. Any desired degree of hardening can easily be obtained by this method.

The effect of the hardening compounds is ascertained from the melting point of the layers, which can be determined as follows:

The layer cast on a substrate is half dipped in water which is continually heated to keep it at a temperature of 100° C. The temperature at which the layer runs off its substrate (formation of streaks) is taken as the melting point or melting off point. When examined by this method, pure protein layers and gelatine layers containing no hardeners never show any increase in melting point. The melting off point under these conditions is in the region of 30° C to 35° C.

The degree of swelling is determined gravimetrically after 10 minutes' treatment in distilled water at 22° C. It is characterised by the swelling factor as follows:

$$\frac{\text{Weight of wet layer}}{\text{Weight of dry layer}} = \text{Swelling factor}$$

To determine the wet scratch resistance, a metal tip of specified size is passed over the wet layer and loaded with a mass of progressively increasing weight. The wet scratch resistance is given as the weight at which the tip leaves a visible scratch trace on the layer. A high weight corresponds to a high wet scratch resistance.

EXAMPLE 1

Compounds 1–41 were used to prepare 5% aqueous solutions, or saturated aqueous solutions if they were not sufficiently soluble. The following strips were half dipped into these solutions for 10 seconds:

a. A strip (1 × 10 cm) of a gelatine layer 10μ in thickness mounted on a cellulose triacetate substrate in which were dispersed 20% by weight of a cyan coupler of the formula

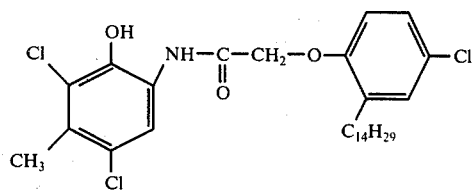

and b. a strip of gelatine layer 10μ in thickness on a cellulose triacetate substrate containing 18% by weight of a soluble cyan coupler of formula

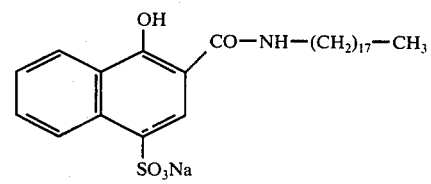

The strips were then dried in a blast of warm air. They were then halved lengthwise and one half of each strip was immediately dipped into water heated to 80° C while the other half was dipped into water at 80° C after 24 hours' storage. The following results were obtained:

Among the strips which has been immediately treated with hot water, those which contained compounds 10, 14, 15, 22, 28 and 40 were found to be only slightly hardened and the layers became detached after a few seconds while the layers of all the other samples remained on their substrates.

Among the samples which has been rinsed with hot water after 24 hours' drying, only the one taken from series (b) and treated with a solution of compound 39 was found to be insufficiently hardened while all the other layers were able to withstand the hot water treatment.

Strips which had been treated for comparison with a 2% solution of formaldehyde or a 2% solution of trisacryloyl hexahydrotriazine showed no signs of hardening in the instant test.

EXAMPLE 2

Strips of gelatine layers similar to those used in Example 1(a) were treated with 0.01 molar aqueous solutions of the compounds indicated in the Table below and dried as indicated in Example 1. The layer melting points, swelling factors and wet strengths of the samples were then determined. The results are shown in the Table.

For comparison, two samples of the same unhardened gelatine layer were dipped, one for 1 minute and the other for 3 minutes, into a 2.5% solution of trisacryloylhexahydro-s-triazine (A) and anothr two were similarly dipped into mucochloric acid (B) and the layer melting point was determined as described above.

The results obtained are shown in the following Table (SF = swelling factor, WS = wet strength):

| Compound | Concentration of solution molar | Properties after the solution had been left to stand: | | | | | | | | |
|---|---|---|---|---|---|---|---|---|---|---|
| | | Fresh solution (30 min) | | | 3 hours | | | 24 hours | | |
| | | Mp | SF | WS | Mp | SF | WS | Mp | SF | WS |
| 1 | 0.01 m | >100 | 2.6 | 650 | >100 | 2.6 | 550 | >100 | 2.9 | 550 |
| 2 | 0.02 m | >100 | 2.4 | 850 | >100 | 2.5 | 850 | >100 | 2.5 | 850 |
| 3 | 0.01 m | >100 | 2.7 | 600 | >100 | 3.0 | 550 | >100 | 3.1 | 550 |
| 4 | 0.01 | >100 | 3.1 | 450 | >100 | 2.9 | 450 | >100 | 3.1 | 350 |
| 5 | 0.01 | >100 | 3.1 | 450 | >100 | 3.2 | 400 | >100 | 3.3 | 300 |
| 6 | 0.01 | >100 | 3.2 | 450 | >100 | 3.2 | 450 | >100 | 3.4 | 350 |
| 7 | 0.01 | >100 | 3.4 | 300 | >100 | 3.4 | 300 | >100 | 3.3 | 300 |
| 8 | 0.01 | >100 | 3.3 | 350 | >100 | 3.6 | 350 | >100 | 3.6 | 350 |
| 9 | 0.01 | >100 | 3.6 | 150 | >100 | 3.6 | 150 | >100 | 3.6 | 150 |
| 12 | 0.01 | >100 | 3.0 | 700 | >100 | 3.2 | 550 | >100 | 3.0 | 550 |
| 13 | 0.01 | >100 | 3.1 | 400 | >100 | 3.3 | 350 | >100 | 3.4 | 350 |
| 16 | 0.01 | >100 | 3.6 | 550 | >100 | 2.8 | 550 | >100 | 3.1 | 450 |
| 21 | 0.01 | >100 | 2.8 | 450 | >100 | 3.0 | 450 | >100 | 3.1 | 450 |
| 24 | 0.01 | >100 | 2.7 | 450 | >100 | 2.8 | 450 | >100 | 2.9 | 450 |
| 25 | 0.01 | >100 | 2.9 | 450 | >100 | 2.9 | 450 | >100 | 3.5 | 350 |

The results obtained in Example 3 demonstrate the excellent stability of the aqueous solutions of the compounds according to the invention even after 1 day's storage. This proves beyond doubt that the compounds are sufficiently stable for industrial use.

EXAMPLE 4

An unsensitized silver bromide emulsion layer was applied to a polyethylene backed paper substrate coated

| Compound No. | Concentration of aqueous solution | Layer Melting Point after | | Swelling factor after | | Wet strength after | |
|---|---|---|---|---|---|---|---|
| | | drying | 1 day | 1 day | 3 days | 1 day | 3 days |
| 1 | 2.08 % | 10' 100° | >100° | 2.6 | 2.7 | 650 p | 650 p |
| 2 | 2.7 % | >100° | >100° | 2.7 | 2.8 | 600 p | 600 p |
| 3 | 2 % | >100° | >100° | 2.8 | 2.9 | 500 p | 500 p |
| 4 | 2.2 % | >100° | >100° | 2.9 | 2.8 | 500 p | 500 p |
| 5 | 2.4 % | >100° | >100° | 3.1 | 3.3 | 450 p | 400 p |
| 6 | 2.9 % | >100° | >100° | 3.2 | 3.3 | 450 p | 400 p |
| 7 | 2.5 % | >100° | >100° | 3.4 | 3.4 | 300 p | 300 p |
| 9 | 3 % | >100° | >100° | 3.6 | 3.5 | 150 p | 300 p |
| 12 | 2.6 % | >100° | >100° | 3.0 | 3.0 | 700 p | 600 p |
| 13 | 2.8 % | >100° | >100° | 3.1 | 3.1 | 600 p | 500 p |
| 16 | 2.4 % | >100° | >100° | 2.6 | 2.7 | 550 p | 650 p |
| 17 | 2.8 % | >100° | >100° | 3.1 | 3.2 | 450 p | 500 p |
| 21 | 2.8 % | >100° | >100° | 2.8 | 2.9 | 450 p | 550 p |
| 24 | 2.2 % | >100° | >100° | 2.7 | 3.0 | 450 p | 450 p |
| 25 | 2.4 % | >100° | >100° | 2.9 | 3.1 | 450 p | 550 p |
| 26 | 2.4 % | 37° | >100° | 3.5 | 3.2 | 350 p | 450 p |
| 27 | 2.7 % | >100° | >100° | 4.0 | 3.8 | 200 p | 250 p |
| 28 | 2.4 % | 37° | >100° | 3.6 | 3.2 | 450 p | 500 p |

| Comparison Sample | Layer Melting Point after Drying |
|---|---|
| A | 35° C |
| B | 35° C |

The results show that gelatine layers which contain the compounds according to the invention harden to become fast to boiling either immediately after drying or at latest after one day's storage, and that no after-hardening takes place.

EXAMPLE 3

Strips of an unhardened gelatine layer of the kind used in Example 1(b) were bathed as indicated in Example 2 in aqueous solutions of compounds of the invention, either when the compounds had been freshly dissolved or after three hours storage of solutions at room temperature or after 24 hours' storage at room temperature. The layers were then dried and their properties determined after 1 day's storage at room temperature.

with adhesive, and the layer was dried. Each of the emulsion layers was hardened by application of a 3% aqueous solution of one of the compounds according to the invention Nos. 1, 2, 4, 5, 6, 12, 13, 18, 24, 25 and 28 and then dried. For comparison, another emulsion layer was hardened with 0.5% of formaldehyde as casting additive and yet another emulsion layer was hardened with 0.5% of the sodium salt of 6-hydroxy-2,4-dichloro-triazine.

The samples were then exposed under a step wedge after 1,3 and 5 days' storage and then processed at 25° C as follows:

Developer 3 g of hydroquinone, 1 g of p-methylaminophenol
13 g of anhydrous sodium sulphite
23 g of anhydrous sodium carbonate
1 g of potassium bromide
water up to 1000 ml
development: 2 minutes at 25° C Short Stop Bath 2% aqueous acetic acid solution, 1 minute at 25° C Fixing Bath 200 g of sodium thiosulphate
20 g of potassium metabisulphite
water up to 1000 ml
treatment: 5 minutes at 25° C Rinsing 15 minutes at 20° C.

The following results were obtained: When compounds 1, 2, 4, 5, 6, 12, 13, 18, 24 and 25 were used, the sensitivity was constant after one day; in the case of compound 28 the sensitivity was constant after 3 days. Swelling and sensitivity underwent no further change.

In samples which had been hardened with formaldehyde and methalkoxydichlorotriazine, a reduction in sensitivity was still found to take place after 8 days. Both the final sensitivity and the maximum density were virtually identical in all samples.

It follows from these results that the compounds according to the invention make it possible for the final hardness to be obtained rapidly and give rise to photographic products which have a constant sensitivity over a longer period of storage.

EXAMPLE 5

A reversal film was prepared by applying the following layers in succession to a cellulose triacetate substrate:

1. A red sensitive silver iodobromide emulsion (70 g of gelatine, 32 g of silver (96% AgBr, 4% AgI) per kg), 6 g of cyan coupler of the formula

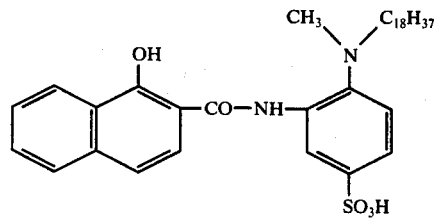

and 24 g of a cyan coupler of the formula

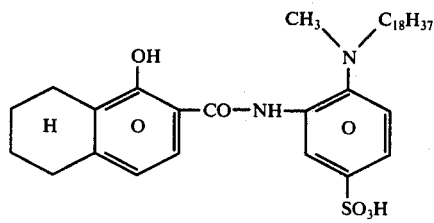

silver application. 1.1 g/m²; 2. an intermediate layer containing 3 g of polymeric white coupler of the following formula per kg of casting solution:

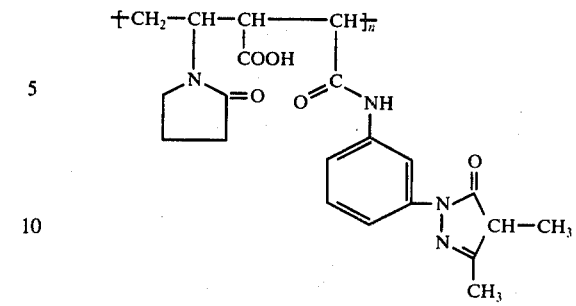

3. a green sensitized silver iodobromide emulsion (96% AgBr, 4% AgI) containing per kg of emulsion 70 g of gelatine, 32 g of silver, 25 g of a magenta coupler of the formula

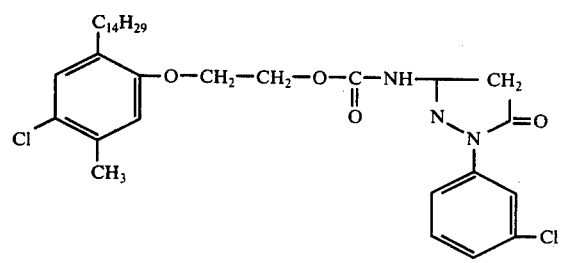

silver application 0.9 g/m²;

4. a yellow filter layer containing colloidal silver obtained from 1.8 g of silver nitrate in 12 g of gelatine per 1000 ml, colour density 0.6 (measured behind blue filter);

5. an unsensitized silver iodobromide emulsion having an iodide content of 2% and containing per kg 110 g of gelatine, 70 g of silver and 45 g of a yellow coupler of the formula

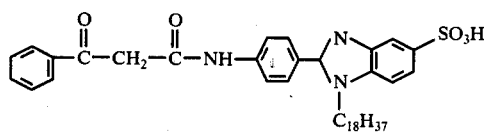

silver application 1.3 g/m².

One sample of the multilayer material obtained in this way was hardened by application of a 2% solution of compound 1 and another sample by application of a 2% solution of the sodium salt of 6-hydroxy-2,4-dichlorotriazine according to German Offenlegungsschrift No. 1,284,290.

Another reversal material was prepared from a similar arrangement of layers except that the red sensitized and the green sensitized emulsion layers as well as the intermediate layers contained 0.4% of 1,3,5-tris-acryloyl-hexahydrotriazine, based on the quantity of gelatine, and the unsensitized layer contained 0.6% of tris-acryloyl-hexahydrotriazine as hardener.

Three materials were obtained and samples from each material were exposed behind a graduated wedge after storage for one day, 8 days and 28 days, respectively, at room temperature, and the exposed materials were processed by a reversal process.

One other sample of each material was conditioned to a moist atmosphere at 35° C and 80% relative humidity for 3 days. Processing: 20° C Black and white developer: (7 minutes):

300 ml of distilled water
2 g of sodium hexametaphosphate
2.3 g of p-methylaminophenol
50 g of anhydrous sodium sulphite
6.6 g of hydroquinone
50 g of anhydrous sodium carbonate
1.5 g of potassium thiocyanate
1.8 g of potassium bromide
0.008 g of potassium iodide
made up to 1000 ml with water: pH 10.
 Short stop bath: (5 minutes)
300 ml of distilled water
30 g of crystalline sodium acetate
5 ml of acetic acid
made up to 1000 ml with water: pH 5.
 Rinsing: 10 minutes
 Reversal exposure: 2 minutes
 Colour development: 18 minutes:
300 ml of distilled water
2 g of nitrilotriacetic acid
3.5 g of N,N-diethyl-p-phenylenediamine
20 g of trisodium phosphate
0.7 g of potassium bromide
0.8 g of hydroxylamine hydrochloride
made up to 1000 ml with water: pH 11.7
 Rinsing: 5 minutes
 Bleaching bath: 5 minutes:
8 g of potassium ferricyanide
20 g of potassium bromide
12 g of disodium phosphate
made up to 1000 ml with water, adjusted to pH 5.2 with acetic acid
 Rinsing: 5 minutes
 Fixing bath: 5 minutes:
150 g of ammonium thiosulphate
10 g of anhydrous sodium sulphite
2 g of sodium hexametaphosphate
made up to 1000 ml with water: pH 7
 Final rinsing: 5 minutes.

Photographic examination showed that the sample which had been hardened with compound 1 attained its final sensitivity after only 1 day and had been hardened fast to boiling. No loss in sensitivity due to after-hardening could be detected.

The sample which had been hardened with the sodium salt of 6-hydroxy-2,4-dichlorotriazine had a melting point of 40° C after 1 day and it was only after 8 days that the combination of layers was fast to boiling and even then it still showed evidence of after-hardening and a loss of sensitivity over the next 28 days.

The sample which had been hardened with the conventional hardener tris-acryloyl-hexahydrotriazine was found to have a layer melting point of around 40° C after 1 day and after 8 days, and the sample which had been hardened for 28 days showed a distinct reduction in sensitivity compared with the fresh sample. The general sensitivity of the fresh sample was higher than that of the material which had been hardened with compound 1.

All three samples had the same sensitivity after 3 days storage in a moist atmosphere.

We claim:

1. A process for providing a photographic material comprising at least one silver halide emulsion associated with at least one supported layer containing protein as a binder in which the protein-containing layer is contacted with an effective amount of hardener to harden the layer wherein the improvement comprises the hardener is a 1-sulphonyl-4-amino-pyridinium salt of the following general formulae:

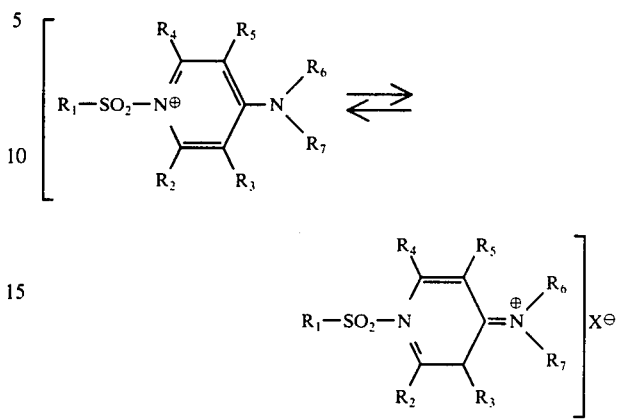

in which
 $R_1$ represents alkyl with 1 to 4 carbon atoms, aryl optionally substituted by halogen, aralkyl, a sulphoalkyl or sulphoalkenyl group with 3 to 4 carbon atoms or a dialkylamino group in which the alkyl portion contains 1 to 3 carbon atoms,
 $R_2$ represents hydrogen or alkyl,
 $R_3$ has the same meaning as $R_2$ or it represents an aminocarbonoyl group or together with $R_2$ it represents the atoms required to complete a condensed benzene ring,
 $R_4$ and $R_5$ represent hydrogen or alkyl,
 $R_6$ represents hydrogen, alkyl with 1 to 3 carbon atoms, aralkyl or sulphoalkyl,
 $R_7$ represents hydrogen or alkyl with 1 to 3 carbon atoms or together with $R_6$ and the nitrogen atom it represents the atoms required to complete a saturated heterocyclic 5-membered or 6-membered ring, and
 $X^-$ represents halogen +, $R_1-SO_3^-$ or a hard anion from the group $ClO_4'$, $BF_4'$, $PF_6'$ or $Sbf_6'$, $X^-$ being absent if $R_1$ or $R_6$ contains a sulpho group.

2. Process according to claim 1, characterised in that the protein-containing layer is coated with a solution of the hardener, and the layer is subsequently dried.

3. Process according to claim 1, characterised in that the hardeners are incorporated in preliminary hardening baths for treating the protein-containing layer before the photographic material is processed.

4. Process according to claim 1, characterised by the use of the hardeners for hardening layers which contain as binders gelatine and carboxyl-containing homopolymers and copolymers.

5. Process according to claim 1, characterised in that the hardeners are applied from aqueous solution.

6. Process according to claim 1, characterised in the hardeners are applied from alcoholic solution.

7. Process according to claim 1, characterised in that the hardeners are applied from aqueous-alcoholic solution.

8. Process according to claim 1, characterised in that the hardeners are used in the casing solution for the layer to be hardened in quantities of from 0.5 to 10% by weight, preferably 1 to 5% by weight, based on the weight of the protein-containing binder.

9. In the process as claimed in claim 2, including a thickener in the hardening solution.

10. In the process as claimed in claim 1 in which the protein-containing layer is included in a multi-layered color photographic material.